(12) United States Patent
Jones et al.

(10) Patent No.: US 7,753,878 B2
(45) Date of Patent: Jul. 13, 2010

(54) SAFETY NEEDLE WITH LOCKOUT MECHANISM

(75) Inventors: Scott Jones, University City, MO (US); George Clark, Lewis Center, OH (US)

(73) Assignee: Tyco Healthcare Group LP, Mansfield, MA (US)

( * ) Notice: Subject to any disclaimer, the term of this patent is extended or adjusted under 35 U.S.C. 154(b) by 389 days.

(21) Appl. No.: 11/525,316

(22) Filed: Sep. 22, 2006

(65) Prior Publication Data

US 2007/0066937 A1    Mar. 22, 2007

Related U.S. Application Data

(60) Provisional application No. 60/719,761, filed on Sep. 22, 2005.

(51) Int. Cl.
*A61M 5/00* (2006.01)
(52) U.S. Cl. ..................................... 604/110
(58) Field of Classification Search ............. 604/110
See application file for complete search history.

(56) References Cited

U.S. PATENT DOCUMENTS

| | | |
|---|---|---|
| 4,183,246 A | 1/1980 | Reynolds |
| 4,676,783 A | 6/1987 | Jagger et al. |
| 4,690,675 A | 9/1987 | Katz |
| 4,747,831 A | 5/1988 | Kulli |
| 4,781,692 A | 11/1988 | Jagger et al. |
| 4,813,426 A | 3/1989 | Haber et al. |
| 4,820,282 A | 4/1989 | Hogan |
| 4,900,307 A | 2/1990 | Kulli |
| 4,900,311 A | 2/1990 | Stern et al. |
| 4,973,316 A | 11/1990 | Dysarz |
| 4,994,034 A | 2/1991 | Botich et al. |
| 5,084,030 A | 1/1992 | Byrne et al. |
| 5,085,639 A | 2/1992 | Ryan |
| 5,088,982 A | 2/1992 | Ryan |
| 5,108,376 A | 4/1992 | Bonaldo |
| 5,114,410 A | 5/1992 | Batlle |
| 5,120,320 A | 6/1992 | Fayngold |
| 5,125,414 A | 6/1992 | Dysarz |
| 5,129,884 A | 7/1992 | Dysarz |
| 5,147,327 A | 9/1992 | Johnson |

(Continued)

FOREIGN PATENT DOCUMENTS

EP    1 221 305 B1    10/2005

(Continued)

OTHER PUBLICATIONS

International Search Report (Form PCT/ISA/210 (first & second sheet) (Apr. 2005) for International Appln. No. PCT/US06/37278, filed Sep. 22, 2006.

*Primary Examiner*—Nicholas D Lucchesi
*Assistant Examiner*—Jason Flick
(74) *Attorney, Agent, or Firm*—Lisa E. Winsor, Esq.

(57) ABSTRACT

A safety needle is provided which includes blocking structure to maintain a sharp tip of a needle safely within a housing and prevent re-advancement of a needle from a safety needle housing. The safety needle includes flexible blocking members positioned on an inner needle assembly which are configured to engage an outer housing after the needle assembly has been fully retracted within the outer housing.

2 Claims, 20 Drawing Sheets

U.S. PATENT DOCUMENTS

| | | | |
|---|---|---|---|
| 5,176,655 A | 1/1993 | McCormick et al. |
| 5,188,119 A | 2/1993 | Sunderland |
| 5,188,599 A | 2/1993 | Botich et al. |
| 5,192,275 A | 3/1993 | Burns |
| 5,226,894 A | 7/1993 | Haber et al. |
| 5,232,456 A | 8/1993 | Gonzalez |
| 5,267,961 A | 12/1993 | Shaw |
| 5,273,540 A | 12/1993 | Luther et al. |
| 5,318,538 A | 6/1994 | Martin |
| 5,330,438 A | 7/1994 | Gollobin et al. |
| 5,338,303 A | 8/1994 | King et al. |
| 5,376,075 A | 12/1994 | Haughton et al. |
| 5,385,551 A | 1/1995 | Shaw |
| 5,389,076 A | 2/1995 | Shaw |
| 5,395,347 A | 3/1995 | Blecher et al. |
| 5,407,431 A | 4/1995 | Botich et al. |
| 5,409,461 A | 4/1995 | Steinman |
| 5,423,758 A | 6/1995 | Shaw |
| 5,501,675 A | 3/1996 | Erskine |
| 5,538,508 A | 7/1996 | Steyn |
| 5,549,571 A | 8/1996 | Sak |
| 5,554,130 A | 9/1996 | McDonald et al. |
| 5,562,629 A | 10/1996 | Haughton et al. |
| 5,562,634 A | 10/1996 | Flumene et al. |
| 5,573,510 A | 11/1996 | Isaacson |
| 5,575,777 A | 11/1996 | Cover et al. |
| 5,578,011 A | 11/1996 | Shaw |
| 5,591,138 A | 1/1997 | Vaillancourt |
| 5,632,733 A | 5/1997 | Shaw |
| 5,676,658 A | 10/1997 | Erskine |
| 5,695,475 A | 12/1997 | Best, Jr. et al. |
| 5,746,215 A | 5/1998 | Manjarrez |
| 5,779,679 A | 7/1998 | Shaw |
| 5,810,775 A | 9/1998 | Shaw |
| 5,928,199 A | 7/1999 | Nakagami |
| 5,931,815 A | 8/1999 | Liu |
| 5,951,525 A | 9/1999 | Thorne et al. |
| 5,997,512 A | 12/1999 | Shaw |
| 6,015,438 A | 1/2000 | Shaw |
| 6,056,726 A | 5/2000 | Isaacson |
| 6,080,137 A | 6/2000 | Pike |
| 6,090,078 A | 7/2000 | Erskine |
| 6,096,005 A | 8/2000 | Botich et al. |
| 6,179,812 B1 | 1/2001 | Botich et al. |
| 6,210,371 B1 | 4/2001 | Shaw |
| 6,221,055 B1 | 4/2001 | Shaw et al. |
| RE37,439 E | 11/2001 | Firth et al. |
| 6,494,863 B1 | 12/2002 | Shaw et al. |
| 6,524,276 B1 | 2/2003 | Halseth et al. |
| 6,547,762 B1 | 4/2003 | Botich et al. |
| 6,572,584 B1 | 6/2003 | Shaw et al. |
| 6,582,402 B1 | 6/2003 | Erskine |
| 6,620,136 B1 * | 9/2003 | Pressly et al. ......... 604/164.08 |
| 6,641,555 B1 | 11/2003 | Botich et al. |
| 6,673,047 B2 | 1/2004 | Crawford et al. |
| 6,743,186 B2 | 6/2004 | Crawford et al. |
| 6,773,419 B2 | 8/2004 | Crawford et al. |
| 6,786,875 B2 | 9/2004 | Barker et al. |
| 6,835,190 B2 | 12/2004 | Nguyen |
| 6,860,872 B2 | 3/2005 | Teichert |
| 6,905,478 B2 | 6/2005 | Ingram et al. |
| 6,945,960 B2 | 9/2005 | Barker et al. |
| 6,972,002 B2 | 12/2005 | Thorne |
| 6,976,976 B2 | 12/2005 | Doyle |
| 7,037,292 B2 | 5/2006 | Carlyon et al. |
| 2003/0040717 A1 | 2/2003 | Saulenas et al. |
| 2003/0078540 A1 | 4/2003 | Saulenas et al. |
| 2003/0093035 A1 * | 5/2003 | Mohammed ................ 604/195 |
| 2003/0199830 A1 | 10/2003 | Nguyen |
| 2003/0220619 A1 | 11/2003 | Polidoro et al. |
| 2004/0193110 A1 | 9/2004 | Giambattista et al. |
| 2004/0267200 A1 | 12/2004 | Carlyon et al. |

FOREIGN PATENT DOCUMENTS

WO      WO 00/47256      8/2000

* cited by examiner

SAFETY NEEDLE WITH LOCKOUT MECHANISM

CROSS REFERENCE TO RELATED APPLICATION:

This patent application claims priority to U.S. Provisional Application Ser. No. 60/719,761, filed Sep. 22, 2005, which is incorporated herein in its entirety by reference.

BACKGROUND

1. Technical Field

The present disclosure relates to the field of safety needles having retraction structure. More particularly, the present disclosure relates to safety needles incorporating lockout mechanisms to prevent re-advancement of an associated needle after initial use and retraction 2. Background of Related Art Hypodermic needles are used for venous access in a variety of medical procedures requiring fluid sampling, percutaneous medication injection, or other delivery to or withdrawal of fluid from a patient. Various intravenous needle assemblies are known which can generally include blood collection needles, infusion needles, hemodialysis needles, needles associated with blood collection bags, etc. Problems associated with the use of intravenous needles may include needlestick injury, stabilization of the needle on a patient, and ease of insertion and withdrawal of the needle from the patient.

Some of the health risks associated with hazardous needle exposure include HIV, hepatitis, and other blood-borne pathogens. Medical professionals are in danger of contracting such blood-borne pathogens from infected patients by inadvertent needle sticks from needles contaminated during medical, dental, laboratory etc. procedures.

Various protective devices including sheaths, have been used to shield sharp tips of needles in order to alleviate danger of needlestick injury to a user. Additionally, many needle devices include the provision of an automatic retraction system to shield the needle within a housing associated with the needle assembly after use. Examples of devices including spring-loaded retraction mechanisms which have no provision for preventing inadvertent, premature retraction include U.S. Pat. No. 5,423,758 to Shaw, U.S. Pat. No. 5,779,679 to Shaw, U.S. Pat. No. 6,096,005 to Botich, U.S. Pat. No. 6,179,812 B1 to Botich and U.S. Pat. No. 6,210,371 B1 to Shaw.

Unfortunately, the same automatic retraction system that is designed to protect the user from needlestick injury may inadvertently be reversed to re-extend the needle from a housing and thereby still pose a threat of needlestick injury. Furthermore, in many systems, an entire needle system is movable within an outer housing and is retracted due to the action of the spring between the outer housing and the needle system. It is possible that a user could accidentally grasp the outer housing and push against the bias of the spring to re-extend the needle.

Therefore, it would be desirable to provide a safety needle which includes a blocking or lockout structure to prevent re-advancement of a needle through and out of the needle housing after the needle has been used and the retraction system activated. It would be further be desirable to provide a lockout structure which is simple, low-cost, and can be easily manufactured on existing safety needle components.

SUMMARY

The presently disclosed safety needles are configured for use in intravenous procedures. The safety needles generally include an outer tubular member, a hollow hub movably positioned in the outer tubular member and a hollow needle extending distally from the hub. The needles terminate in a sharp tissue piercing tip. A fluid tube extends from the hub and is in fluid communication with the needle. The safety needles further include an automatic retraction system including a spring to bias the hub proximally within the outer tubular member such that the sharp tip of the needle is safely contained within the outer tubular member after use.

The disclosed safety needles include lockout structure for preventing re-advancement of the sharp tip of the needle from the elongate member after the retraction system has biased the needle proximally. In one embodiment, the lockout structure includes a flexible member positioned on the hub. The flexible member is configured to move proximally with the hub through the elongate tubular member and engage a surface of the elongate tubular member to prevent the hub from moving distally relative to the elongate tubular member.

In one embodiment the flexible member is angled distally so as to drag along and inner surface of the outer tubular member and regulate the rate of retraction of the hub effected by a biasing member through the elongate tubular member.

In one embodiment the safety needle includes two flexible members oriented on diametrically opposed sides of the hub.

In one embodiment the safety needle includes two distally facing flexible whiskers which are configured to pass through a passage in the elongate tubular member and flex outwardly so as to engage an outer surface of the elongate tubular member to prevent the hub, and thus the needle tip, from being re-extended from the elongate tubular member.

In another embodiment the safety needle includes a spring biased retraction device having a projection on the hub which is engageable with the housing, to prevent the hub from moving proximally within the elongate tubular housing. The spring biased retraction device may also include a biasing member to urge the projection into engagement with the housing. In one embodiment, the projection is urged into engagement with an inner proximal surface of the housing.

The spring biased retraction device may also include a thumb pad on the hub. The thumb pad is positioned such that pressure on the thumb pad relative to the elongate tubular member disengages the projection from an inner surface of the elongate tubular housing.

There is also disclosed a method of preventing re-advancement of a sharp tip of a safety needle from an associated housing including providing a safety needle have an elongated tubular housing, an inner member movable within the housing and a sharp tissue penetrating needle extending distally from the inner member. A flexible projection is provided on the inner member to engage a surface of the housing. The method includes the step of engaging a surface of the housing with the projection after the tissue penetrating needle has been safely retracted within the housing. In one embodiment, the method includes providing a pair of flexible members movable within the housing and engageable with a proximal outer surface of the housing to securely lock the hub and needle in a proximal most position relative to the housing.

DESCRIPTION OF THE DRAWINGS

Various embodiments of the presently disclosed safety needle are disclosed herein with reference to the drawings, wherein.

DETAILED DESCRIPTION OF EMBODIMENTS

Embodiments of the presently disclosed safety needle device with lockout mechanism will now be described in detail with reference to the drawings wherein like numerals designate identical or corresponding elements in each of the several views. As is common in the art, the term "proximal" refers to a location on the device closer to the user or operator, i.e. surgeon or physician, while the term "distal" refers to a location on the device further away from the user.

Figure 1:
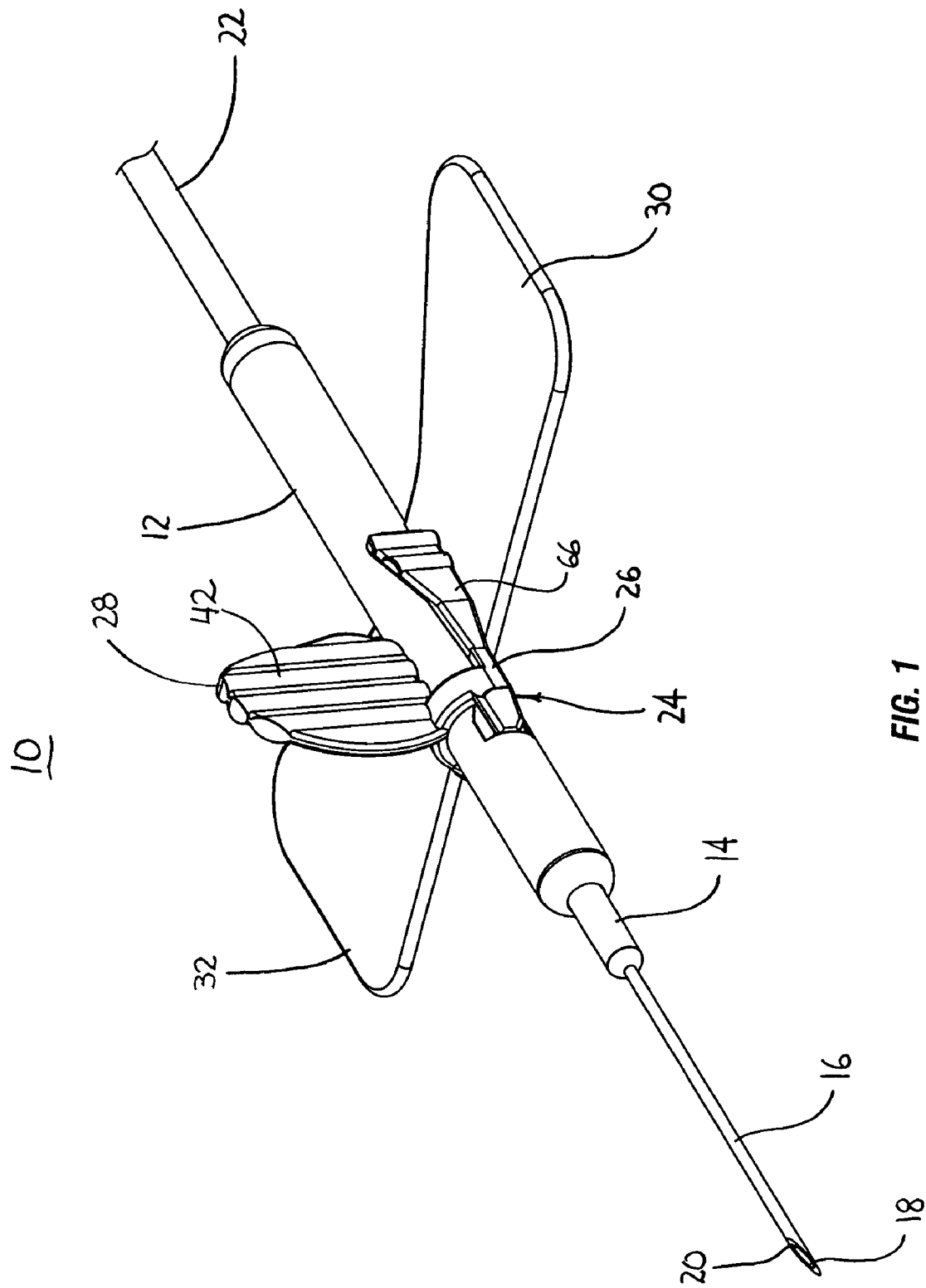
FIG. 1 is a perspective view of one embodiment of a safety needle with a lockout mechanism and a needle in an extended position.
Figure 2:
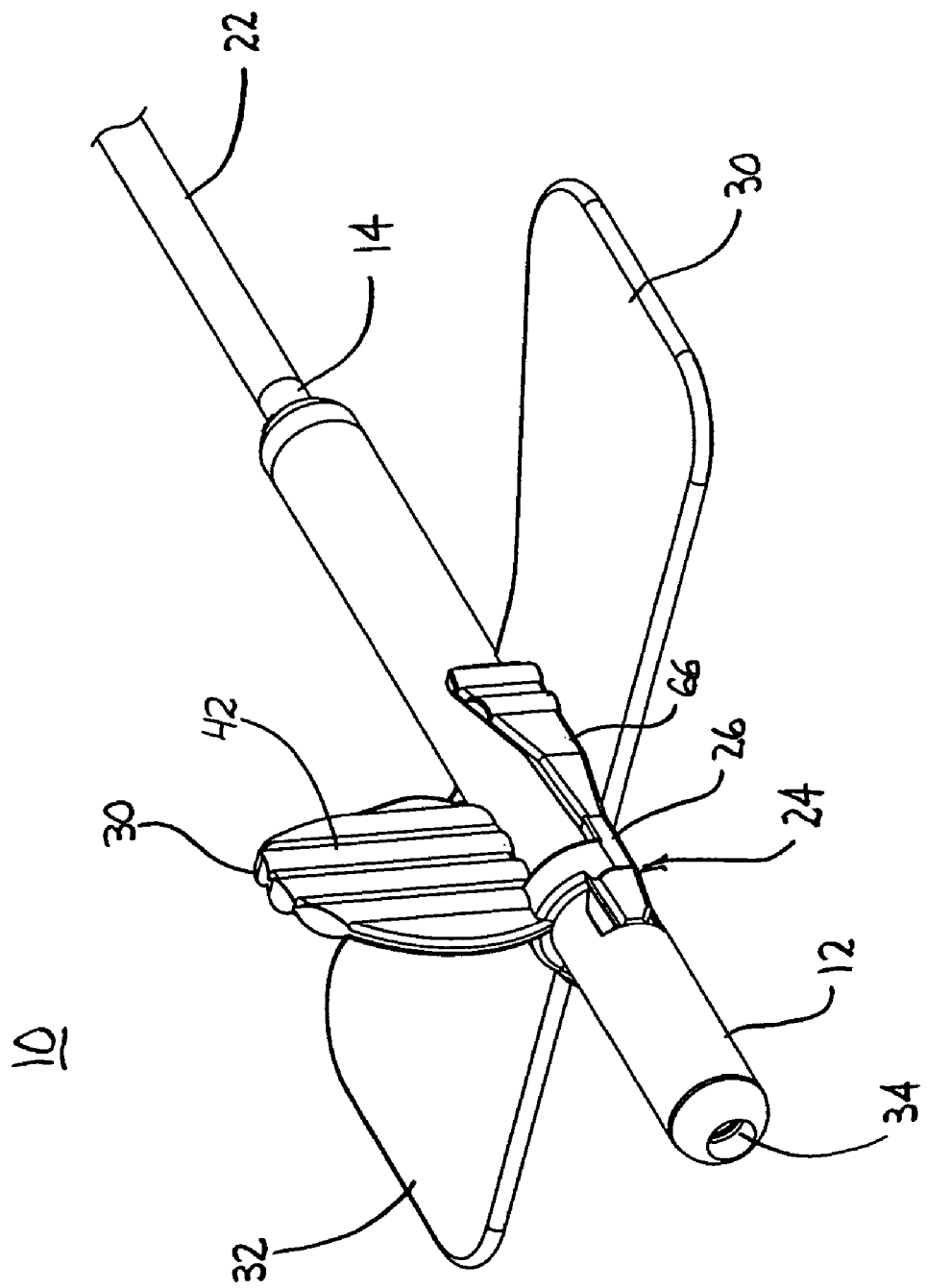
FIG. 2 is a perspective view of the safety needle shown in FIG. 1 with the needle in a retracted position.
Figure 3:
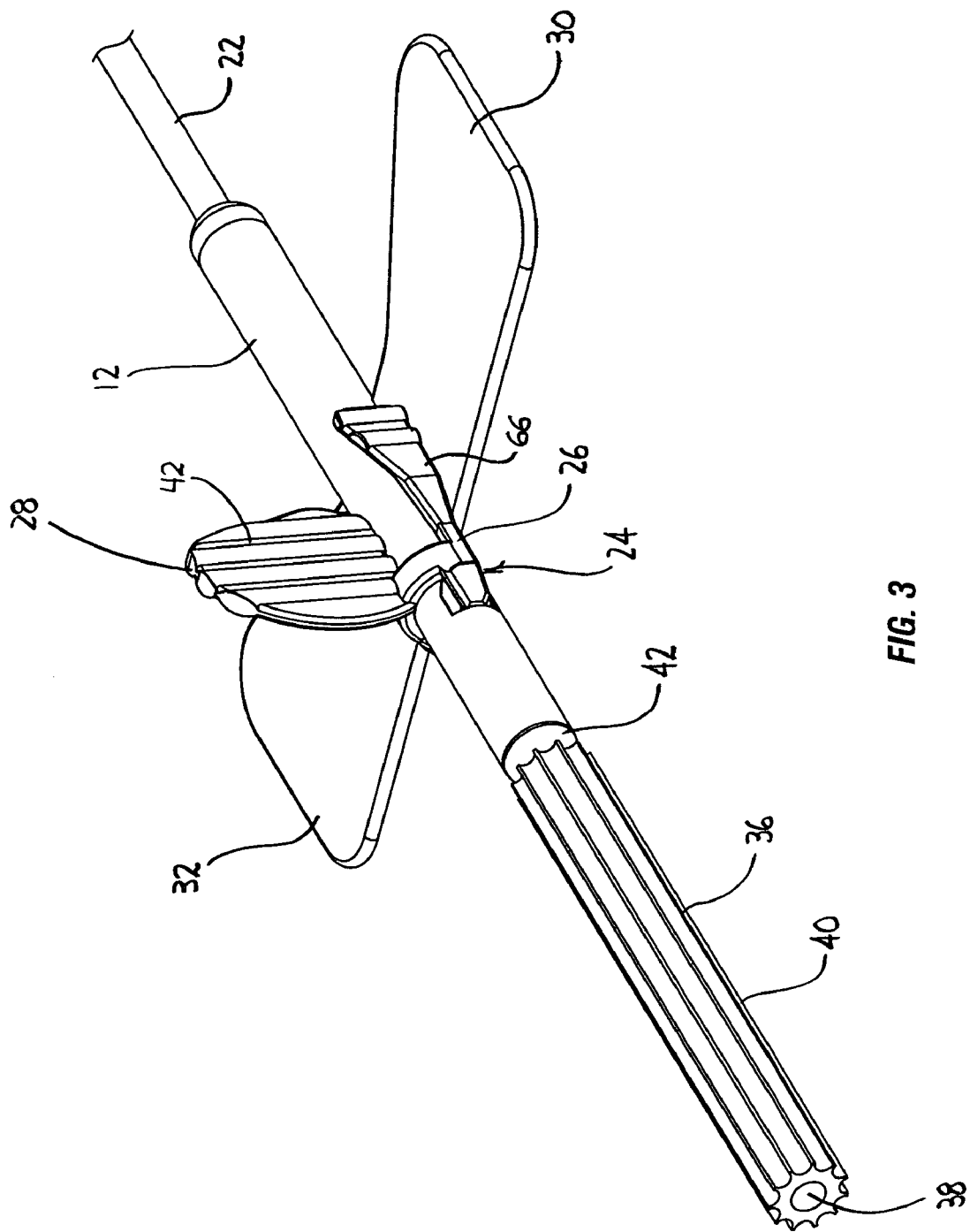
FIG. 3 is a perspective view of the safety needle shown in FIG. 1 with a safety sheath positioned about the needle.

Referring now to FIGS. 1-3, and initially with regard to FIG. 1, there is disclosed one embodiment of a safety needle 10 having a lockout mechanism. Safety needle 10 is of the type generally used during intravenous procedures to insert or withdraw fluid from the body of a patient. Generally, safety needle 10 includes an elongated tubular member 12 having a hub 14 movably mounted therein. A hollow needle 16 extends distally from hub 14 and has a sharp tissue penetrating tip 18 at a distal end 20 of needle 16. Hollow needle 16 is movable with hub 14 within the elongate tubular member 12 so as to be extendable from the elongate tubular member 12 and retractable into elongate tubular member 12 to thereby shield a user from sharp tissue penetrating tip 18. A fluid tube 22 extends from hub 14 and is in fluid communication with needle 16 through hub 14.

Safety needle 10 includes retraction mechanism 24 to retract needle 16 within elongate tubular member 12. A release member 26 of retraction mechanism 24 enables a user to actuate retraction mechanism 24.

Safety needle 10 is further provided with a dorsal fin 28 to facilitate manipulation of safety needle 10 by a user during insertion or withdrawal of needle 16 from a patient. Dorsal fin 28 may be integrally formed with release member 26 or, alternatively, can be affixed to, or integral with, elongate tubular member 12.

Safety needle 10 also includes a pair of wings 30, 32 which stabilize safety needle 10 against the body of the patient. Wings 30, 32 may be either flexible or rigid and may be formed separately from, or integral with, elongate tubular member 12. One or both of wings 30, 32 may be used to facilitate grasping of safety needle 10 during insertion and withdrawal of needle 16 from the body of a patient.

In FIG. 2, safety needle 10 is illustrated with needle 16 in the retracted position. In the retracted position, needle 16 is safely contained within a bore 34 of elongate tubular member 12. In the retracted position, tubular member 12 prevents any needle stick injury to the user as will be described in more detail hereinbelow.

Referring also to FIG. 3, safety needle 10 is illustrated with a safety sheath 36 positioned over needle 16. Safety sheath 36 includes a bore 38 for receipt and protection of needle 16. Safety sheath 36 is designed to protect a user prior to its use in an operation. Safety sheath 36 may also include a ribbed outer surface 40 to facilitate grasping and removal of safety sheath 36 by the user. It is contemplated that safety needle 10 will be manufactured and shipped with safety sheath 36 positioned over needle 16 to prevent needlestick injury to the user prior to its use in an intravenous procedure.

In order to facilitate manipulation of safety needle 10, dorsal fin 28 may also be provided with a ribbed outer surface 42 to provided secure grasping surface by the user. It is contemplated herein that safety needle 10 may be provided with other textured or ribbed services to facilitate manipulation by the user, e.g., knurled, grooved, etc.

Figure 4:
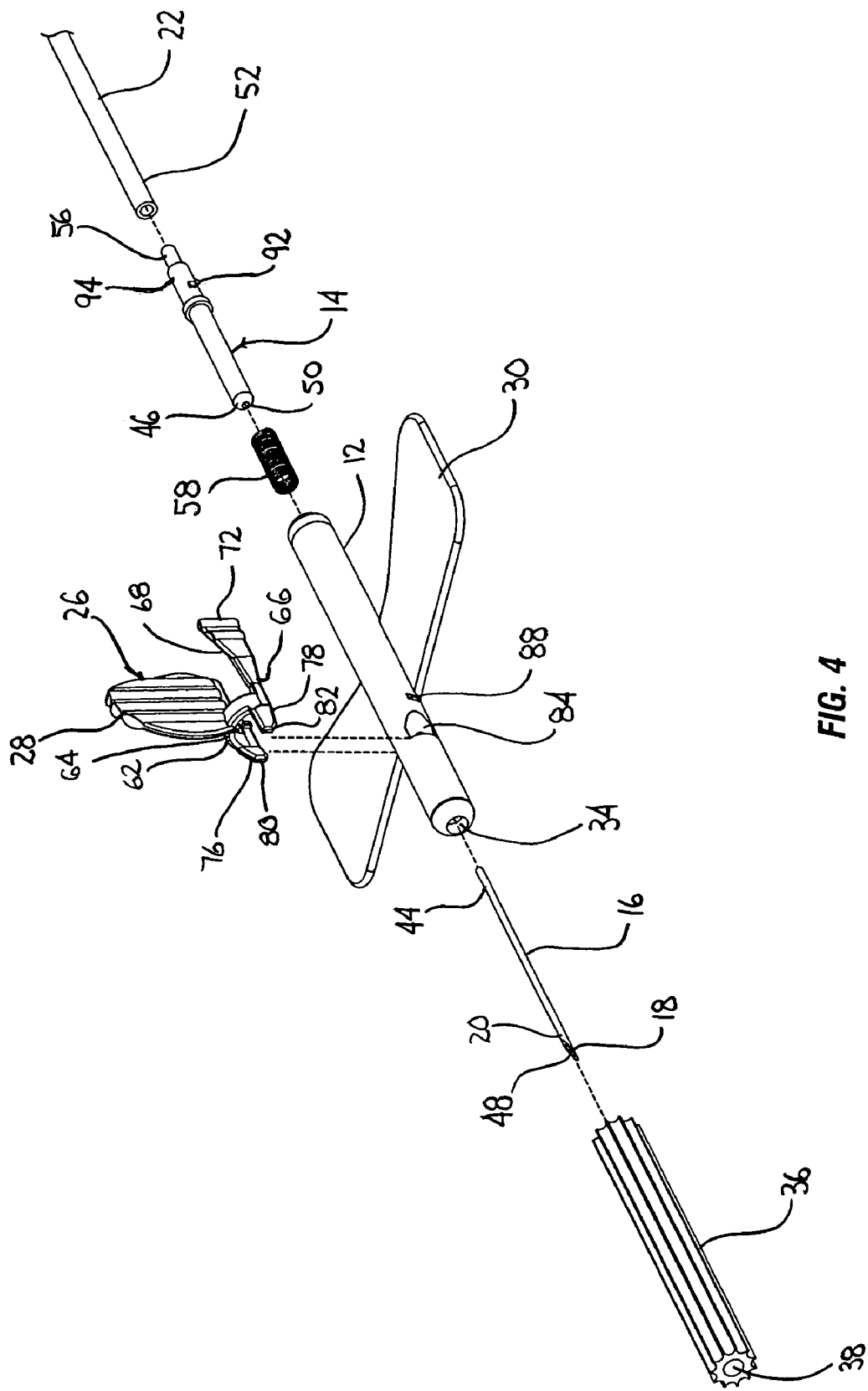
FIG. 4 is a perspective view of the safety needle shown in FIG. 3 with parts separated.
Figure 5:
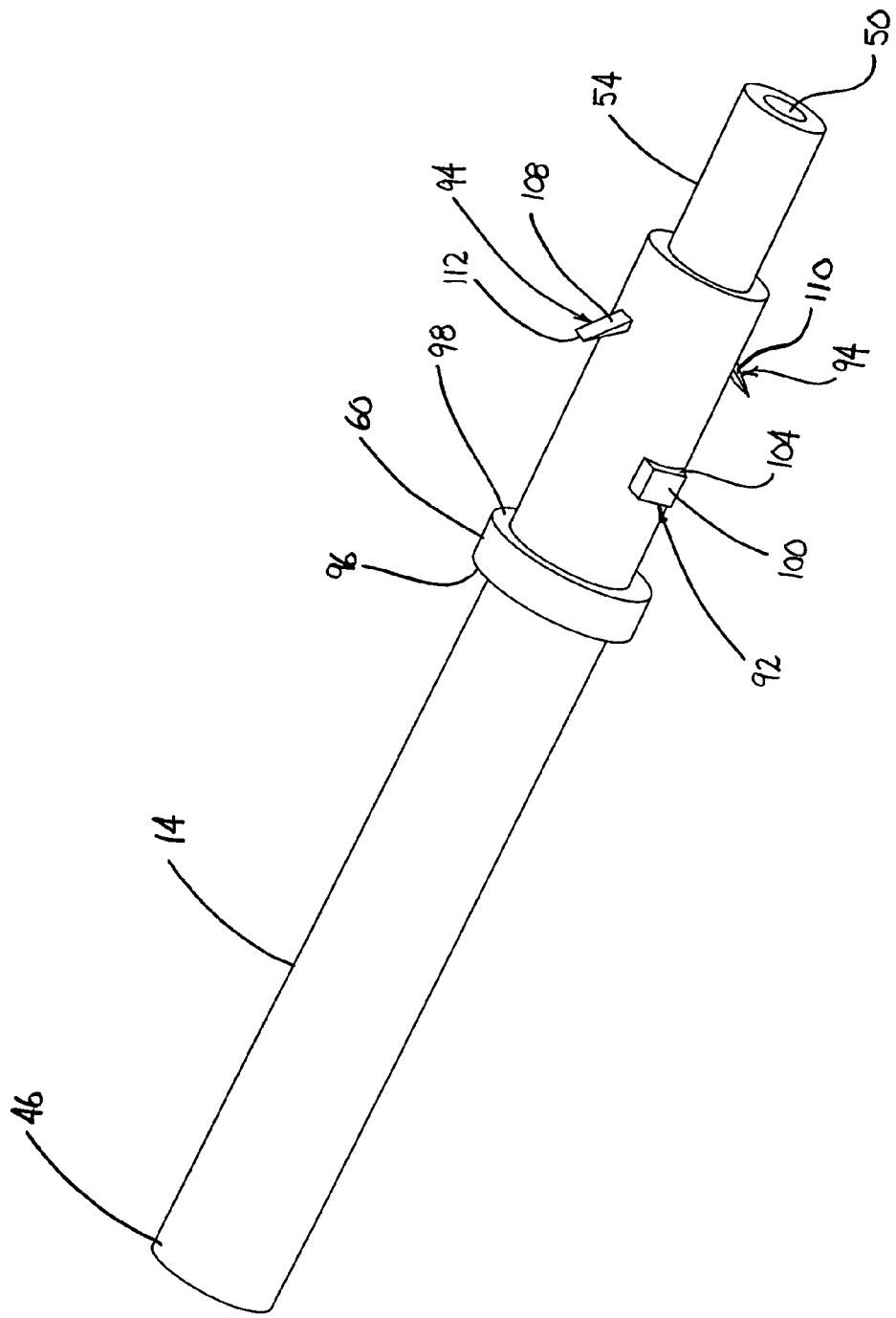
FIG. 5 is a perspective view of a hub of the safety needle shown in FIG. 1.

Referring now to FIGS. 4 and 5, safety needle 10 will now be described in more detail. The proximal end 44 of needle 16 extends through bore 34 of elongate tubular member 12 and is affixed to a distal end 46 of hub 14. As noted above, needle 16 is of the type used during intravenous procedures and includes a throughbore 48 for the transmission of fluids. Hub 14 similarly includes a throughbore 50 for transmission of fluids from needle 16 to fluid tube 22. A first end 52 of fluid tube 22 is affixed over a stepped down portion 54 formed at a proximal end 56 of hub 14.

As noted hereinabove, safety needle 10 includes a retraction mechanism 24 to retract needle 16 within elongate tubular member 12 to prevent needlestick injury to the user. Retraction mechanism 24 includes a spring 58 which is positioned within elongate tubular member 12 about hub 14. Spring 58 is configured to engage a stop collar 60 formed on hub 14 to bias hub 14, and thus needle 16, proximally within elongate tubular member 12 in a manner described in more detail hereinbelow.

Figure 6:
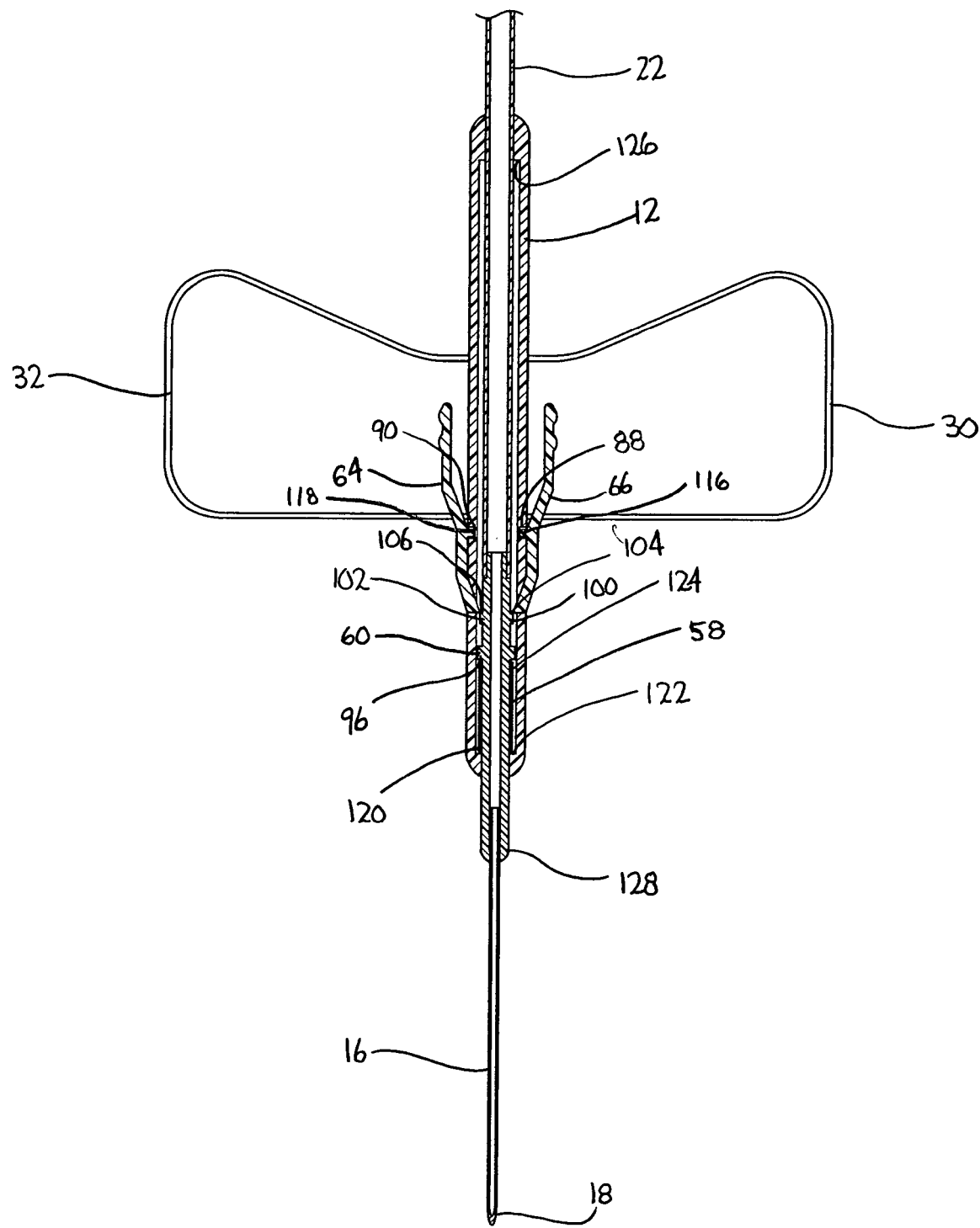
FIG. 6 is a top view, partially shown in section, of the safety needle shown in FIG. 1 with the needle in the extended position.
Figure 7:
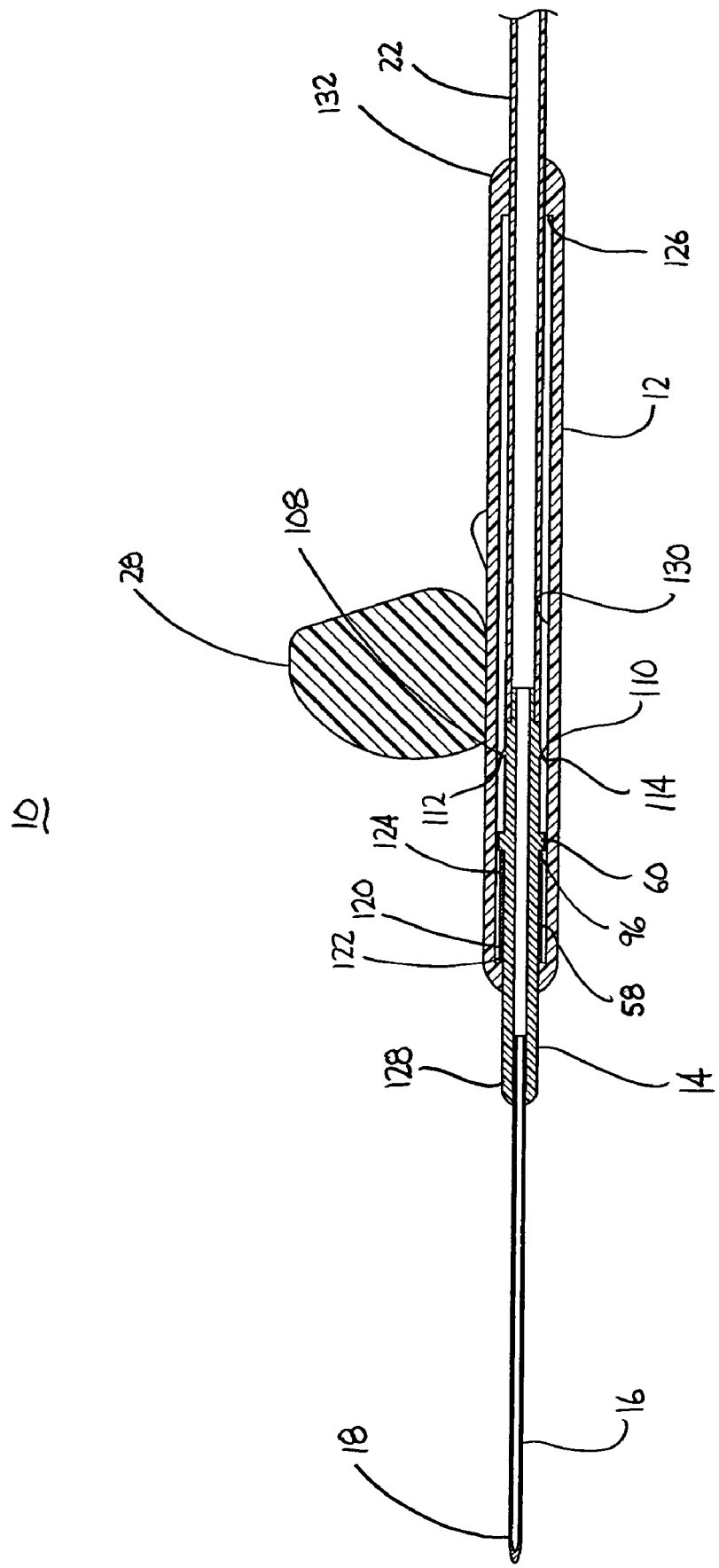
FIG. 7 is a side cross-sectional view of the safety needle shown in FIG. 6 with the needle in the extended position.
Figure 8:
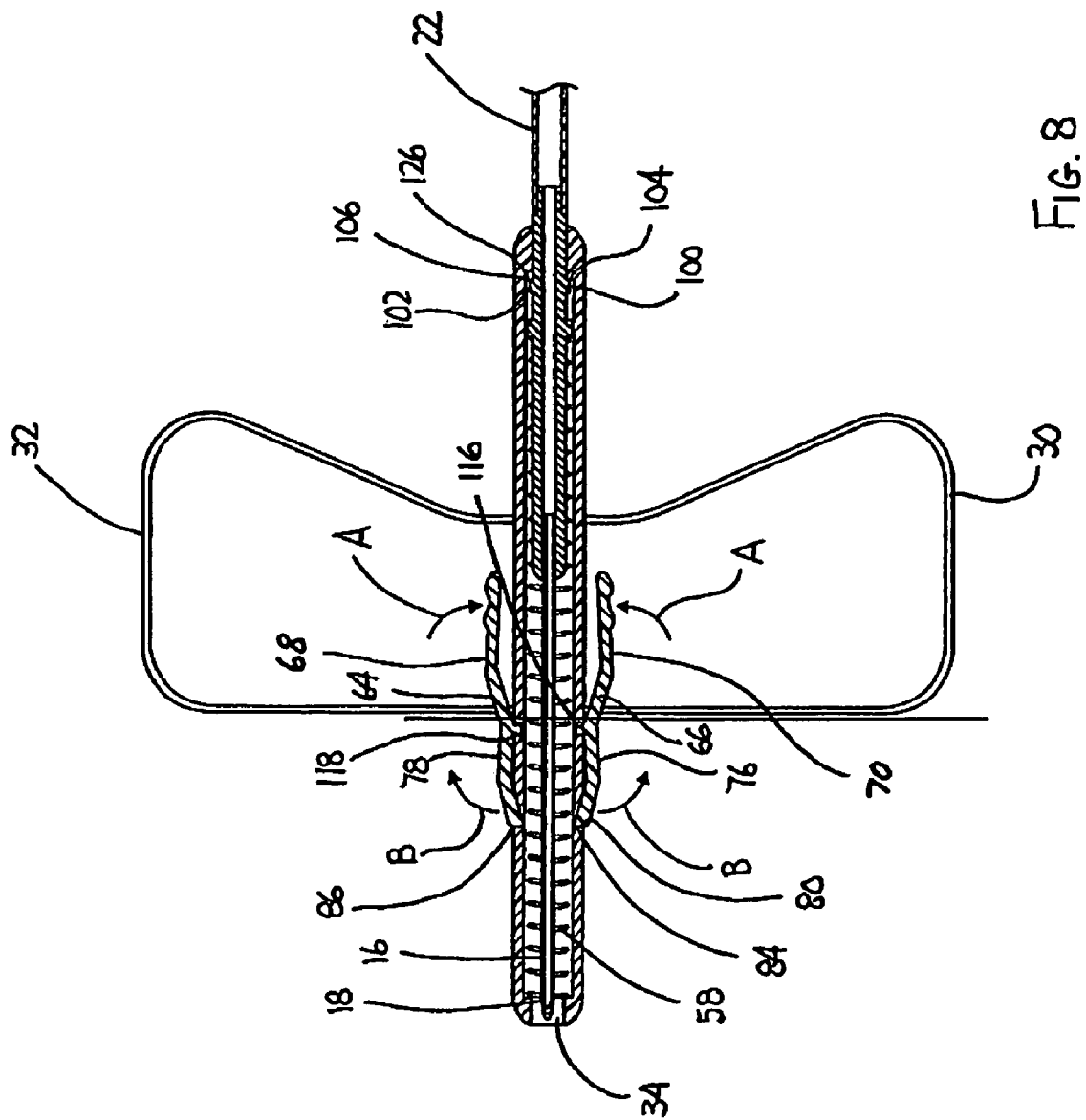
FIG. 8 is a top cross-sectional view with the needle nearing the fully retracted position.

Referring to FIGS. 1-4 and 6-8, release member 26 includes a bridge 62 having a first arm 64 and a second arm 66 positioned on opposed sides of bridge 62. Arms 64 and 66 are flexible about bridge 62. Arm 64 includes a proximal arm section 68 and arm 66 includes a proximal arm section 70 (FIG. 8). Proximal arm sections 68 and 70 are configured to be grasped by the user in order to actuate release member 26. Proximal arm sections 68, 70 may include ribbed surfaces 72, 74 respectively, to facilitate grasping by the user. Arms 64, 66 include distal arm portions 76, 78, respectively which are configured to engage hub 14 and retain hub 14 in an advanced or a distal most position within elongate tubular member 12 against the bias of spring 58. Specifically, distal arm portion 76 includes a lip 80 and distal arm portion 78 includes a lip 82. Distal arms 76 and 78 extend through a pair of cut outs 84, 86 (FIGS. 4 and 8) formed in opposed sides of elongate tubular member 12 such that lips 80, 82 project into bore 34 of elongate tubular member 12. Release member 24 is supported on elongate tubular member 12 in snap fit fashion. A pair of notches 88, 90 are formed on opposed sides of elongate tubular member 12 to retain release member 24 thereon and to provide pivot points for arms 64, 66. Hub 14 is provided with stop structure 92 to engage lips 80, 82 such that lips 80, 82 retain hub 14 in a distal most position within elongate tubular member 12 and against the bias of spring 58. Hub 14 further includes lockout structure 94 which prevents re-advancement of hub 14 after hub 14 has been completely retracted.

Referring now to FIG. 5, further details of hub 14 will now be described. As noted above, collar 60 is provided to engage spring 58 in order to bias hub 14 within elongate tubular member 12. Collar 60 includes a distal facing surface 96 configured to engage spring 58 and proximally facing surface 98.

In order to retain hub 14 in a distal most position against the bias of spring 58, stop structure 92 on hub 14 includes a first engagement block 100 and a second engagement block 102 provided on the opposite side of engagement block 100. Engagement blocks 100, 102 are provided with proximally facing engaging surfaces 104 and 106. When hub 14 is in a distal most position, engaging surfaces 104 and 106 are engaged by a lips 80, 82 of arms 64 and 66 of release member 26 to hold hub 14 in the distal most position. Proximally facing engaging surfaces 104 and 106 provide the further function of limiting the retraction of hub 14 within outer tubular member 12 in a manner described in more detail hereinbelow. Alternately, blocks 100 and 102 could be removed and collar 60 can function to engage lips 80, 82 of release member 26 and limit retraction of hub 14 within outer tubular member 12.

A novel feature of the disclosed safety needle 10 is lockout structure 94 which retains needle 16 in a retracted position within elongate tubular member 12 and prevents any further re-advancement thereof. Specifically, a pair of flexible projections or whiskers 108, 110 (FIG. 5) project radially and angle distally from opposed sides of hub 14. Whiskers 108, 110 are configured to engage an external wall or surface of elongate tubular member 12 so as to block any post retraction distal movement of hub 14 relative to elongate tubular member 12. Whiskers 108 and 110 are sufficiently flexible to move through a proximal most passage in elongate tubular member 12, in a manner described hereinbelow, and expand to engage a proximal most surface of elongate tubular member 12. Whiskers 108 and 110 may be formed integrally with hub 14 or may be provided as a separate structure or structures.

Whiskers 108 and 110 terminate in flexible tips 112 and 114 which are configured to engage and ride along an inner surface of elongate tubular member 12. Flexible tips 112, 114 provide sufficient friction between the inner surface of elongate tubular member 12 and hub 14 so as to control the rate of retraction of hub 14 effected by the bias of spring 58.

Referring now to FIGS. 6 and 7, and initially with regard to FIG. 6, as noted above, arms 64 and 66 are pivotally mounted to elongate tubular member 12. Specifically, arms 64 and 66 are provided with pivot projections 116 and 118. Pivot projections 116, 118 are configured to reside within notches 88 and 90 formed in elongate tubular member 12. Pivot projections 116, 118 secure release member 26 both circumferentially and longitudinally on elongate tubular member 12.

As shown, a distal end 120 of spring 58 engages a distal inner surface 122 of housing 12. Similarly, a proximal end 124 of spring 58 engages distal surface 96 of collar 60 on hub 14 to bias hub 14 proximally relative to elongate tubular member 12.

Elongate tubular member 12 has a proximal facing surface 126 within bore 34 which cooperates with proximal facing surfaces 104 and 106 of engagement blocks 100, 102 to limit the proximal travel of hub 14 within elongate tubular member 12.

In order to observe the flow of fluids through hub 14, hub 14 is provided with a transparent zone 128 (FIG. 7) at a distal end adjacent the proximal end of needle 16. By observing the flow of fluid through transparent zone 128 the user can confirm that needle 16 has been properly positioned within the body.

Referring to FIG. 7, elongate tubular member 12 has an inner surface 130 against which whiskers 108, 110 drag during proximal retraction of needle 16. Elongate tubular member 12 has a proximalmost outer surface 132. Upon full retraction, whiskers 108 and 110 exit bore 34 of tubular member 12 and engage proximal most outer surface 132 to prevent re-advancement of hub 14 within elongate tubular housing 12, and thus prevent re-advancement of needle 16 from bore 34.

With reference to FIGS. 3 and 6-10, the use and operation of safety needle 10 will now be described. As best shown in FIG. 3, safety needle 10 is provided with safety sheath 40 positioned over needle 16 to prevent any needlestick injury to the user during unpackaging and immediately prior to use. Once the user is ready to employ safety needle 10, ribbed outer surface 36 of safety sheath 40 is grasped and safety sheath 40 is removed from needle 16.

Referring now to FIGS. 6 and 7, in the initial position, needle 16 is in the advanced position and extends distally from elongate tubular housing 12. Spring 58 is in a compressed condition between distal inner surface 122 of housing 12 and proximal facing surface 96 of hub 14. Hub 14 is retained in the distal most position by engagement of lips 80, 82 with proximal facing surfaces 104 and 106 of engagement blocks 100,102 (FIG. 6).

Figure 22:
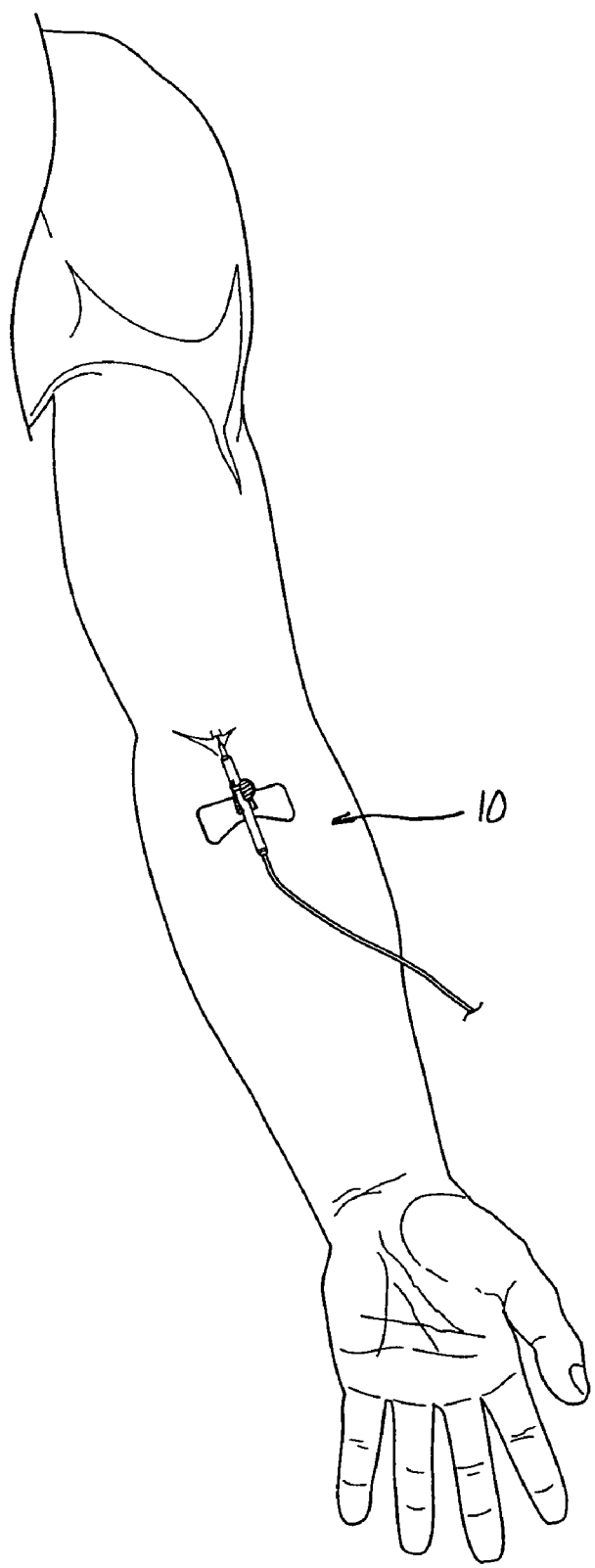
FIG. 22 is a perspective view of the safety needle shown in FIG. 1 with the needle in the extended position inserted into the arm of a patient.

Once safety needle 10 has been unpackaged and safety sheath 36 removed, safety needle 10 is inserted in normal intravenous fashion such that sharp tip 18 penetrates a vein for either infusion, injection or removal of fluids from a patient (See FIG. 22). In order to assist in the insertion of needle 16 of safety needle 10 into the vein of a patient, the user may grasp dorsal fin 28 which is provided to facilitate manipulation of safety needle 10. Alternately, a single wing may be grasped to facilitate of safety needle 10 into a vein. Additionally, as noted hereinabove, in the situation where wings 30 and 32 are flexible, they also may be deformed grasped simultaneously to facilitate insertion of safety needle 10 into a patient. Once safety needle 10 has been inserted into the vein of a patient, the proper positioning of needle 16 within the vein may be verified by observing the flow of fluids through transparent portion 128 of hub 14, i.e., visually confirm operation by observing "flashback".

Referring now to FIG. 8, once the intravenous procedure has been completed, the user can remove needle 16 from the body of the patient. In conjunction with the removal, or soon thereafter, the user may actuate retraction mechanism 24 to a draw sharp tip 18 of needle 16 safely within bore 34 of elongate tubular housing 12. Again, dorsal fin 28 or one or more wings 30, 32 can be grasped to facilitate removal of safety needle 10 from the body of the patient. Retraction mechanism 24 is actuated by squeezing proximal arm 68 and proximal arm 70 inwardly towards housing 12 in the direction indicated by arrows A to rotate arms 64 and 66 about pivot points 116, 118. This rotation of arms 64 and 66 moves distal arms 76 and 78 radially outwardly in the direction of arrows B. As distal arms 76 and 78 move outwardly lips 80 and 82 disengage from proximal facing surfaces 104 and 106 of engagement blocks 100, 102.

Once lips 80, 82 have been disengaged from engagement blocks 100, 102, hub 14 is free to move in a proximal direction against the bias of spring 58. Hub 14 will move distally until proximally facing surfaces 104 and 106 engage proximal inner surface 126 of housing 12. This prevents any further proximal retraction of hub 14 relative to elongate tubular member 12. As noted above, tips 112 and 114 of whiskers 108 and 110 drag along inner surface 130 of elongate tubular member 12 to limit the rate of retraction of hub 14 effected by the bias of spring 58.

As shown, in the proximal most position sharp tip 18 of needle 16 is safely contained within bore 34 of housing 12 to prevent needlestick injury to the user.

As noted hereinabove, safety needle 10 is provided with a novel lockout structure which prevents re-advancement of needle 16 from bore 34 thereby ensuring that there is no accidental needlestick injury to the user.

Figure 9:
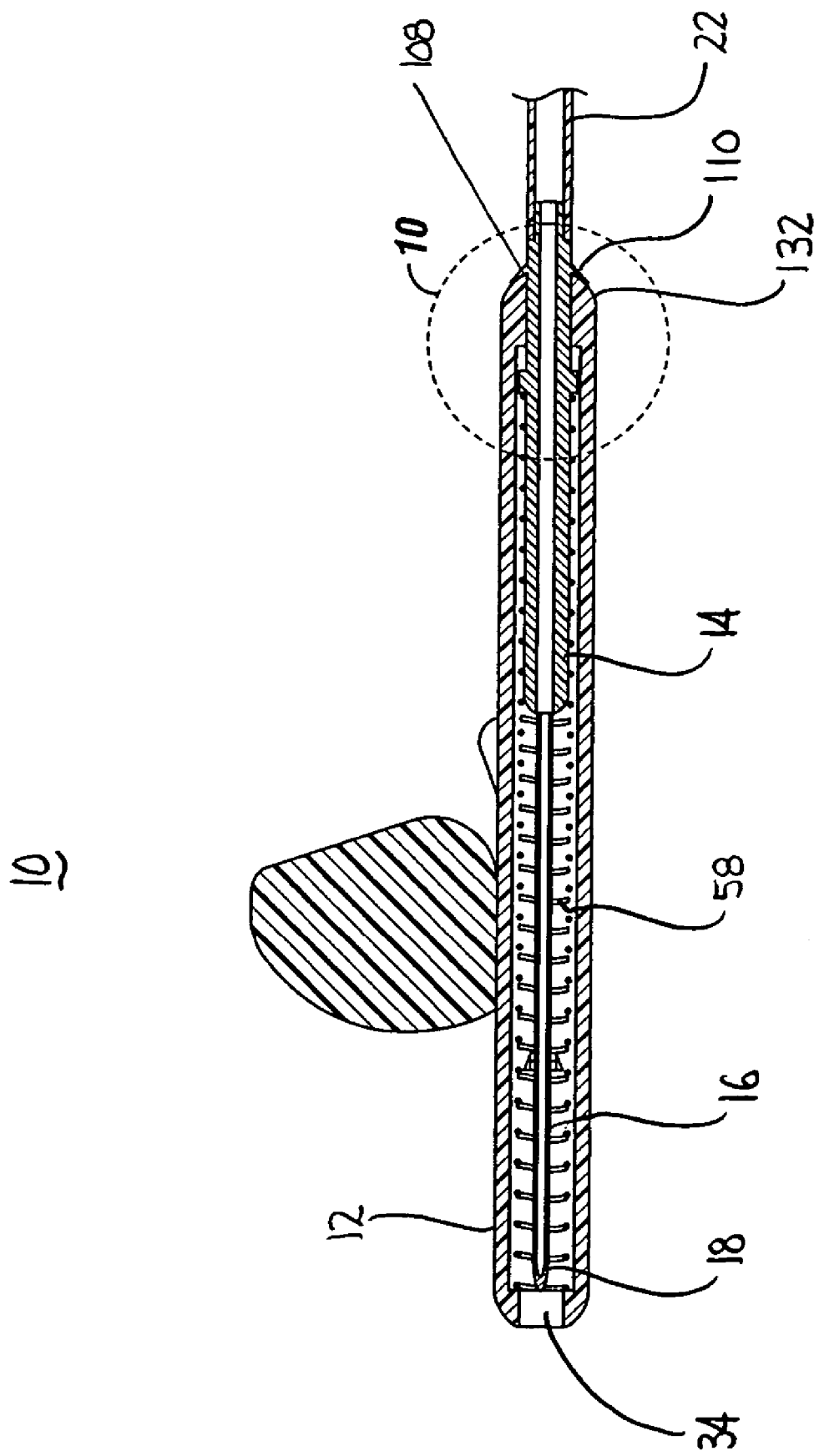
FIG. 9 is a side cross sectional view of the safety needle shown in FIG. 8 with the needle in the fully retracted position and the lockout mechanism engaged.
Figure 10:
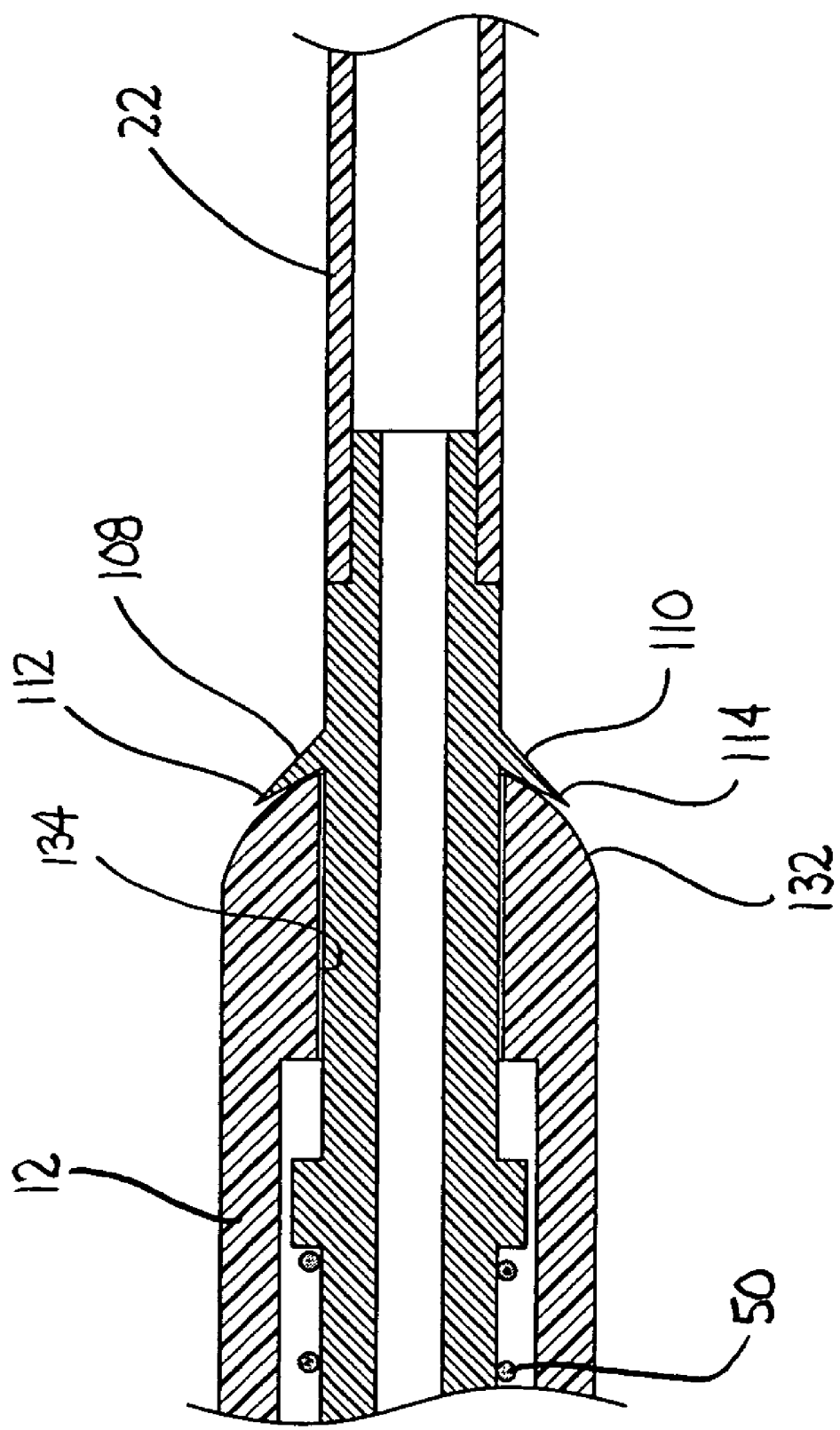
FIG. 10 is an enlarged view of the indicated area of detail shown in FIG. 9.

Referring to FIGS. 9 and 10, once hub 14 has reached a retracted or proximal most position within elongate tubular member 12, whiskers 108 and 110 exit bore 34 and engage proximal facing surface 132 of elongate tubular member 12 to prevent any re-advancement of hub 14 relative to elongate tubular member 12. This, effectively, "locks out" safety needle device 10 against any inadvertent advancement of needle 16.

As best shown in FIG. 10, at proximal end 132 of elongate tubular member 12, bore 34 includes a proximal passageway 134 which has a sufficient inner diameter to allow whiskers 108 and 110 to flex inwardly and pass therethrough. However, this inner diameter of proximal passageway 134 is sufficiently narrow to prevent passage of engagement blocks 100 and 102 therethrough (FIG. 8).

Figure 11:
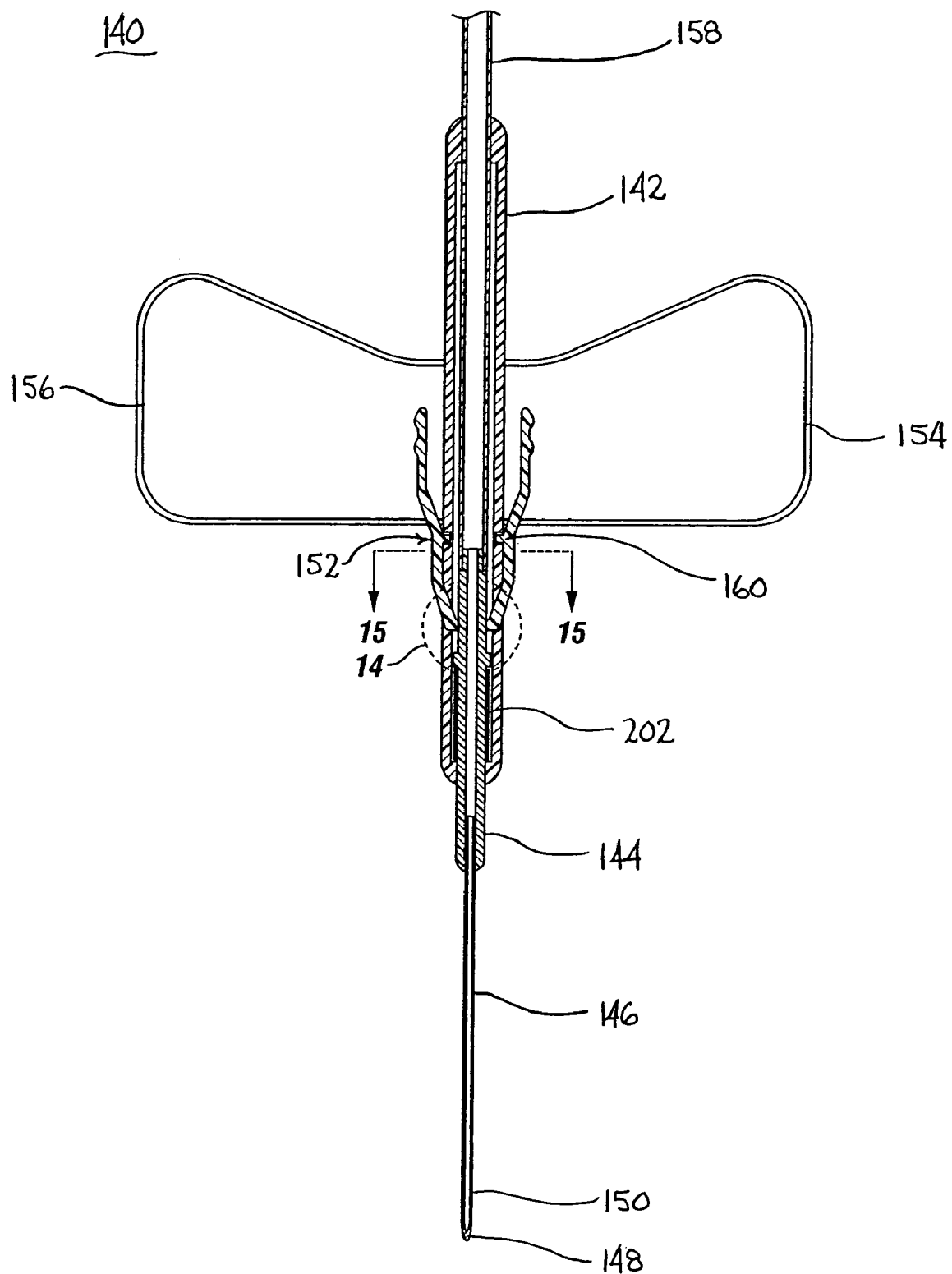
FIG. 11 is a top cross-sectional view of an alternative embodiment of the presently disclosed safety needle with lockout mechanism with the needle in an extended position.

Referring now to FIGS. 11-17, and initially with regard to FIG. 11 there is disclosed an alternative embodiment of a safety needle shown generally as 140. Safety needle 140 is substantially similar to safety needle 10 described hereinabove but has a modified release member/hub interface. Safety needle 140 generally includes an elongate tubular member 142 having a hub 144 movably mounted therein. A needle 146 extends distally from hub 144 and terminates in a sharp tissue piercing tip 148 at a distal end 150. Safety needle 140 includes a retraction mechanism 152. Similar to safety needle 10 described hereinabove, safety needle 140 includes a first wing 154 and a second wing 156 to stabilize safety needle 140 on a patient. A tube 158 extends from hub 144.

Figure 12:
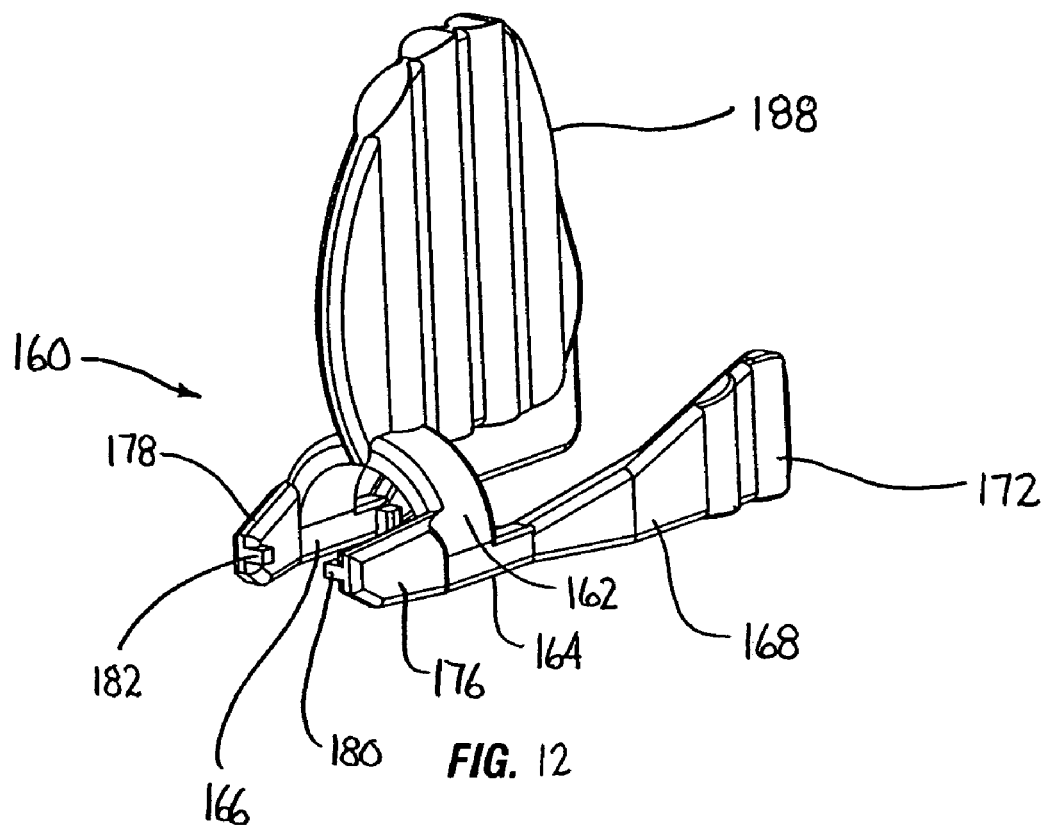
FIG. 12 is a perspective view of a release member of a retraction mechanism and a dorsal fin of the safety needle shown in FIG. 11.
Figure 13:
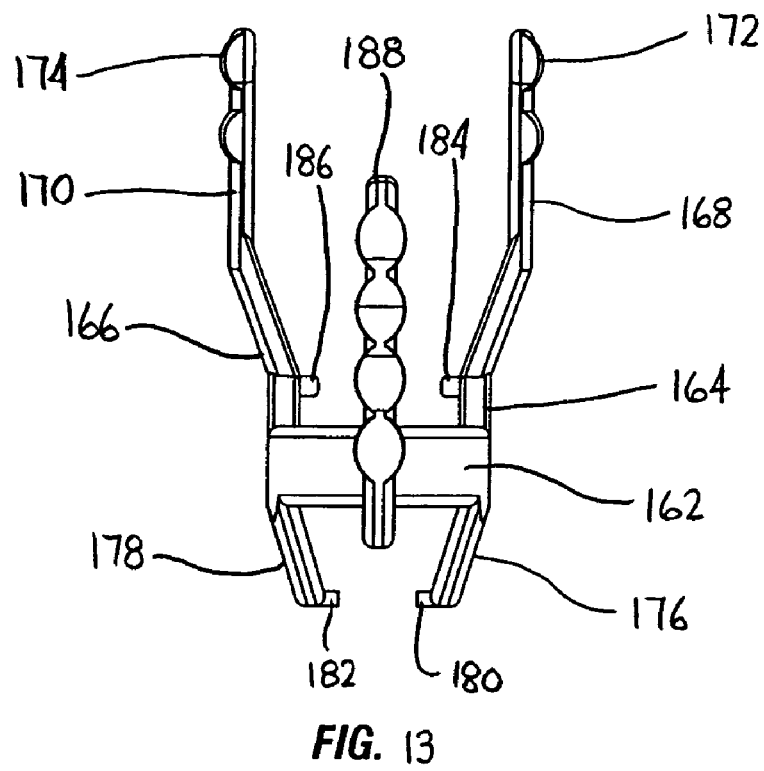
FIG. 13 is a top view of the release member and dorsal fin shown in FIG. 12.

Referring now to FIGS. 12 and 13, there is provided an alternative release member 160. Release member 160 includes a bridge 162 and first and second arms 164 and 166 on opposed sides of bridge 162. Arms 164, 166 include proximal arms 168, 170 respectively. As with the previous embodiment, proximal arm 168 and proximal arm 170 may be supplied with ribbed surfaces 172, 174 respectively to facilitate handling of safety needle 140. Arms 164, 166 include distal arms 176, 178 respectively. As an alternative to lips 80, 82 described hereinabove with respect to release member 26, release number 140 includes inward projections 180, 182 extending inwardly from distal arms 176, 178. Inward projections 180, 182 are configured to engage notches 194 and 196 (FIG. 14) formed in hub 144 to retain hub 144 in a distal most or advanced position relative to elongate tubular member 142. Arms 164, 166 also include pivot points 184, 186 which are configured to engage elongate tubular member 142 substantially as described hereinabove. As with the previous embodiment, safety needle 140 includes a dorsal fin 188 provided on release member 160.

Figure 14:
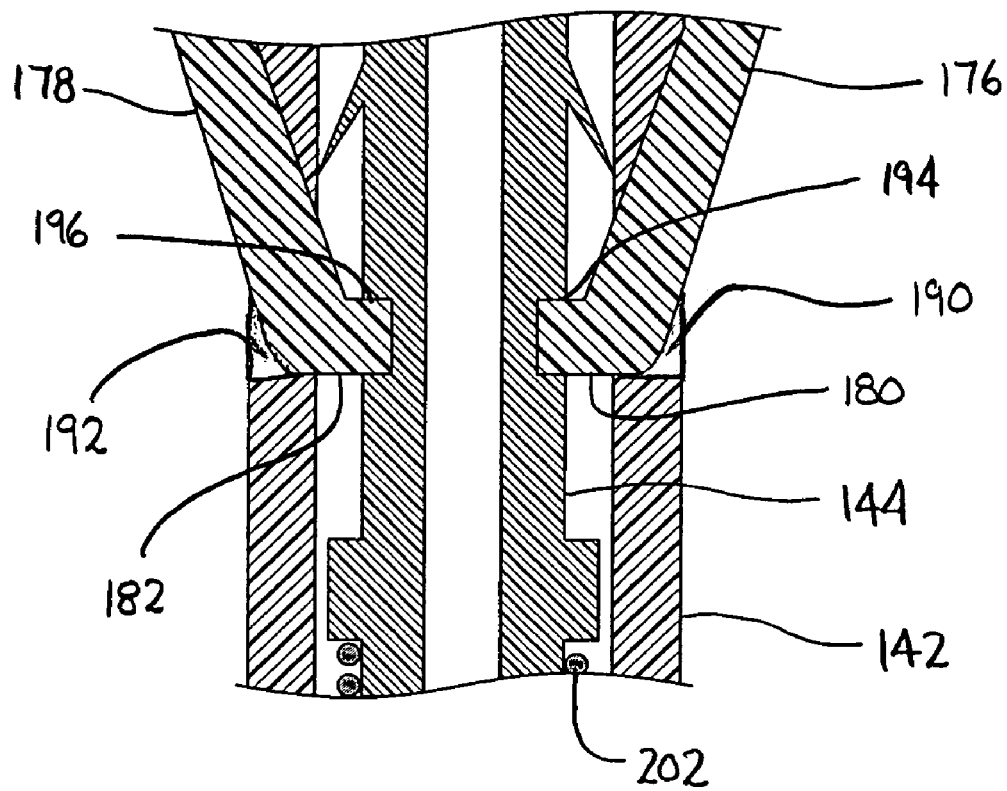
FIG. 14 is an enlarged view of the indicated area of detail shown in FIG. 11.

Referring now to FIG. 14, elongate tubular member 142 is provided with a pair of cut outs 190 and 192 to allow passage of inward projections 180, 182, respectively, therethrough. Cutouts 190 and 192 are aligned with notches 194 and 196. As shown, inward projections 180 and 182 engage notches 194 and 196 in hub 144 to retain hub 144 in a distal most position.

Figure 15:
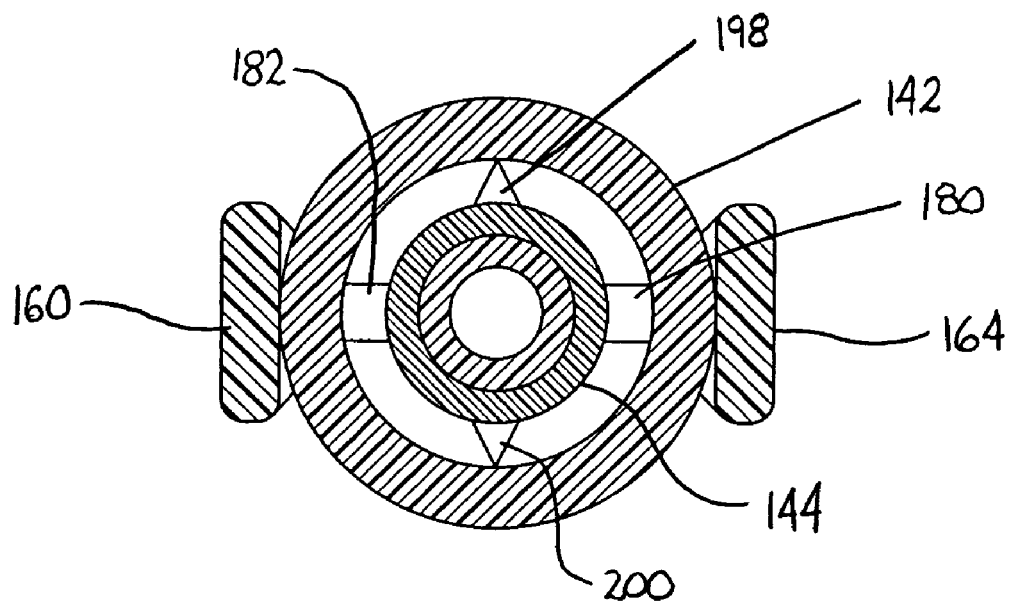
FIG. 15 is a cross-sectional view taken along the section lines 15-15 of FIG. 11.

Referring for the moment to FIG. 15, safety needle 140 has a pair of flexible whiskers 198, 200 provided on hub 144. Whiskers 198, 200 engage elongate outer member 142 in the manner described hereinbelow to prevent re-advancement of hub 144, and thus needle 146, after safety needle 140 has been moved to a retracted position.

Referring again to FIG. 11, safety needle 140 includes a spring 202 to bias hub 144 and needle 146 proximally within elongate tubular member 142.

Figure 16:
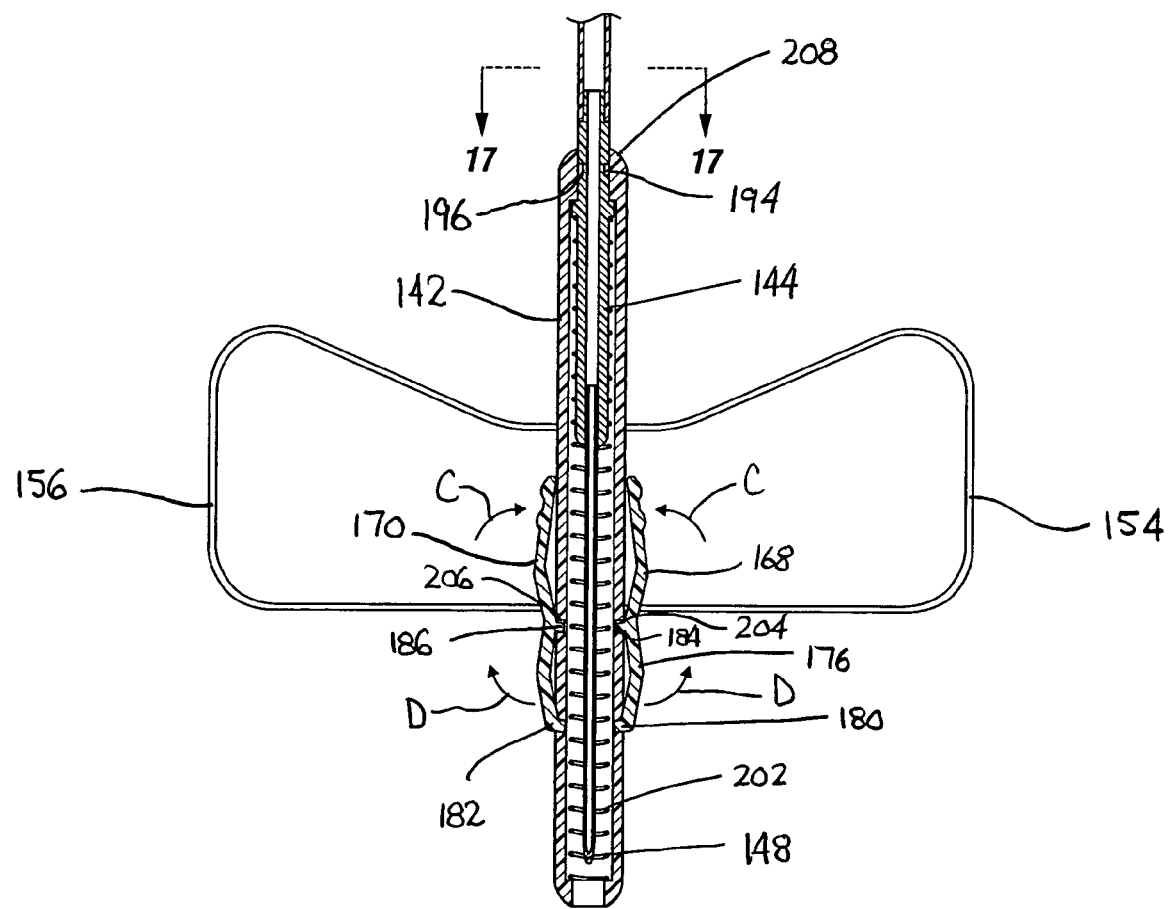
FIG. 16 is a top cross-sectional view of the safety needle shown in FIG. 11 with the needle in the retracted position.

Referring also to FIG. 16, the operation of retraction mechanism 152 (FIG. 11) of safety needle 140 will now be described in detail. When the user wishes to retract needle 146 within elongate tubular member 142, proximal arms 168, 170 are pivoted radially inwardly in the direction of arrows C rotating arms 164, 166 about pivot points 184 and 186. Similar to that described hereinabove with regard to safety needle 10, hub 144 includes a pair of opposed notches 204, 206 for receipt of pivot points 184, 186. Rotation of arms 164, 166 moves distal arms 176, 178 in the direction indicated by arrow D radially outwardly of cut outs 190, 192 in elongate tubular member 142. This motion draws inward projections 180, 182 out of notches 194 and 196 formed in hub 144 allowing hub 144 to retract proximately due to the bias of spring 202.

Figure 17:
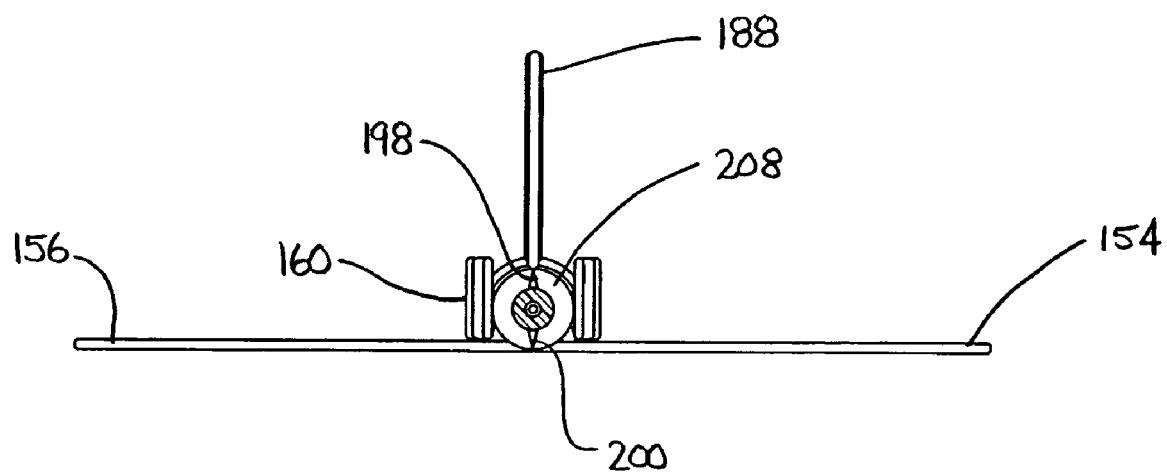
FIG. 17 is a cross-sectional view taken along section lines 17-17 of FIG. 16.

Referring now to FIG. 17, upon full retraction, whiskers 198, 200, engage a proximal surface 208 of elongate tubular housing 142 to "lockout" hub 144 against re-advancement in a manner substantially similar to that described hereinabove with regard to safety needle 10. Collar 60 prevents hub 144 from being pushed from housing 142 (FIG. 11).

Figure 18:
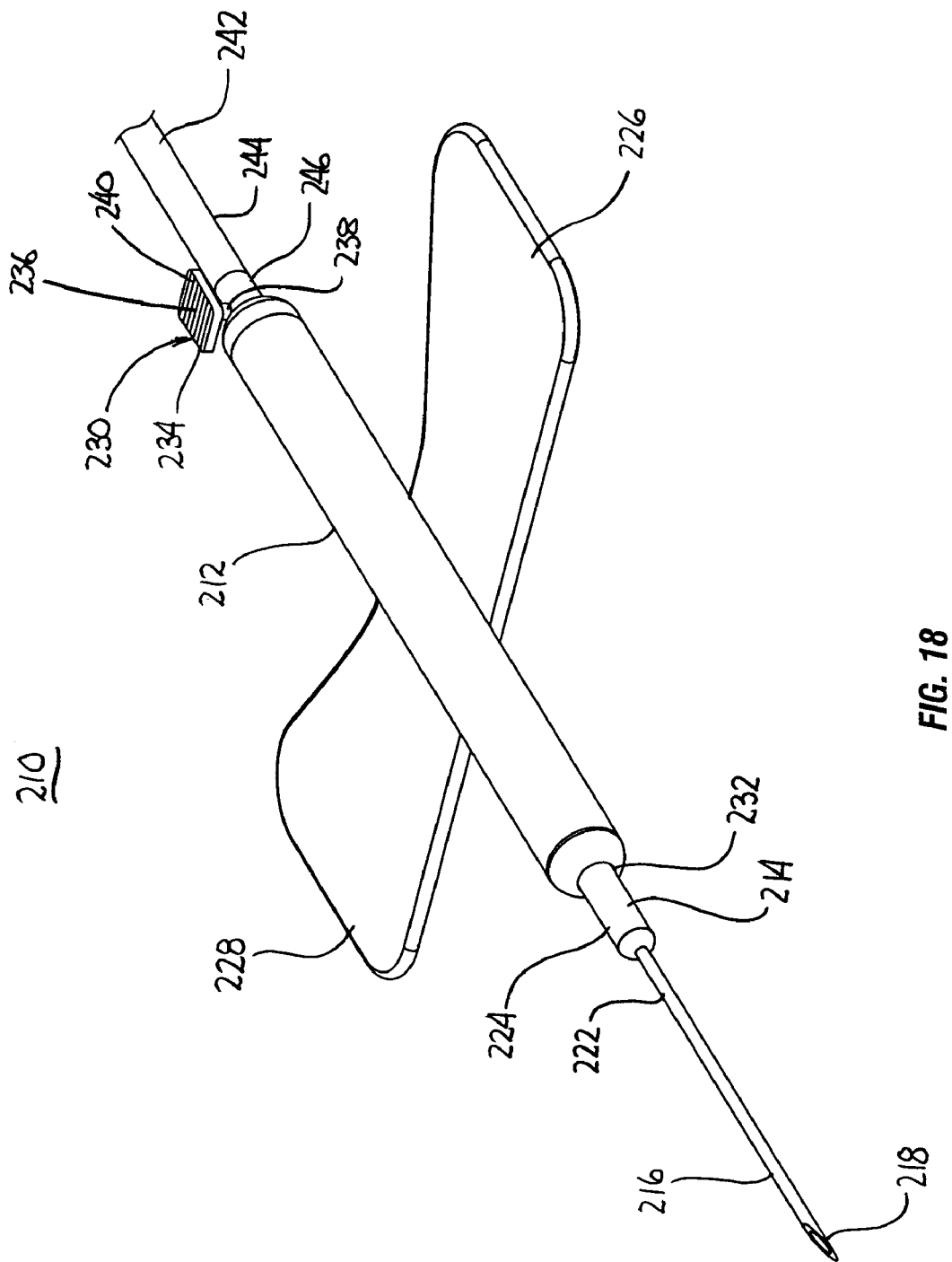
FIG. 18 is a perspective view of another embodiment of the presently disclosed safety needle with a lockout mechanism.

Referring to FIGS. 18-21, and initially with respect to FIG. 18, there is disclosed a alternative embodiment of a safety needle with lockout structure shown generally as 210 having a further alternate retraction mechanism. Safety needle 210 generally includes an elongate tubular member 212 having a hub 214 movably mounted therein. A needle 216 extends distally from hub 214 and terminates in a sharp tissue piercing tip 218 at a distal end 220 thereof. As with prior embodiments, a proximal end 222 of needle 216 is affixed to a distal end 224 of hub 214. Safety needle 210 also includes wings 226, 228 extending from the elongate tubular member 212 to stabilize safety needle 210 on the body of a patient.

Safety needle 210 is provided with a retraction mechanism 230 to retract hub 214 and needle 216 safely within a bore 232 of elongate tubular member 212. Retraction mechanism 230 includes a release member 234. Release member 234 is affixed to hub 214 (FIG. 20) and includes a thumb pad 236 attached to hub 214 by a post 238. Thumb pad 236 may include a ribbed surface 240 to facilitate manipulation by a user. A tube 242 is in fluid communication with needle 216 through hub 214. A first end 244 of tube 242 is affixed to a proximal end 246 of hub 214 in a manner substantially described as above.

Figure 19:
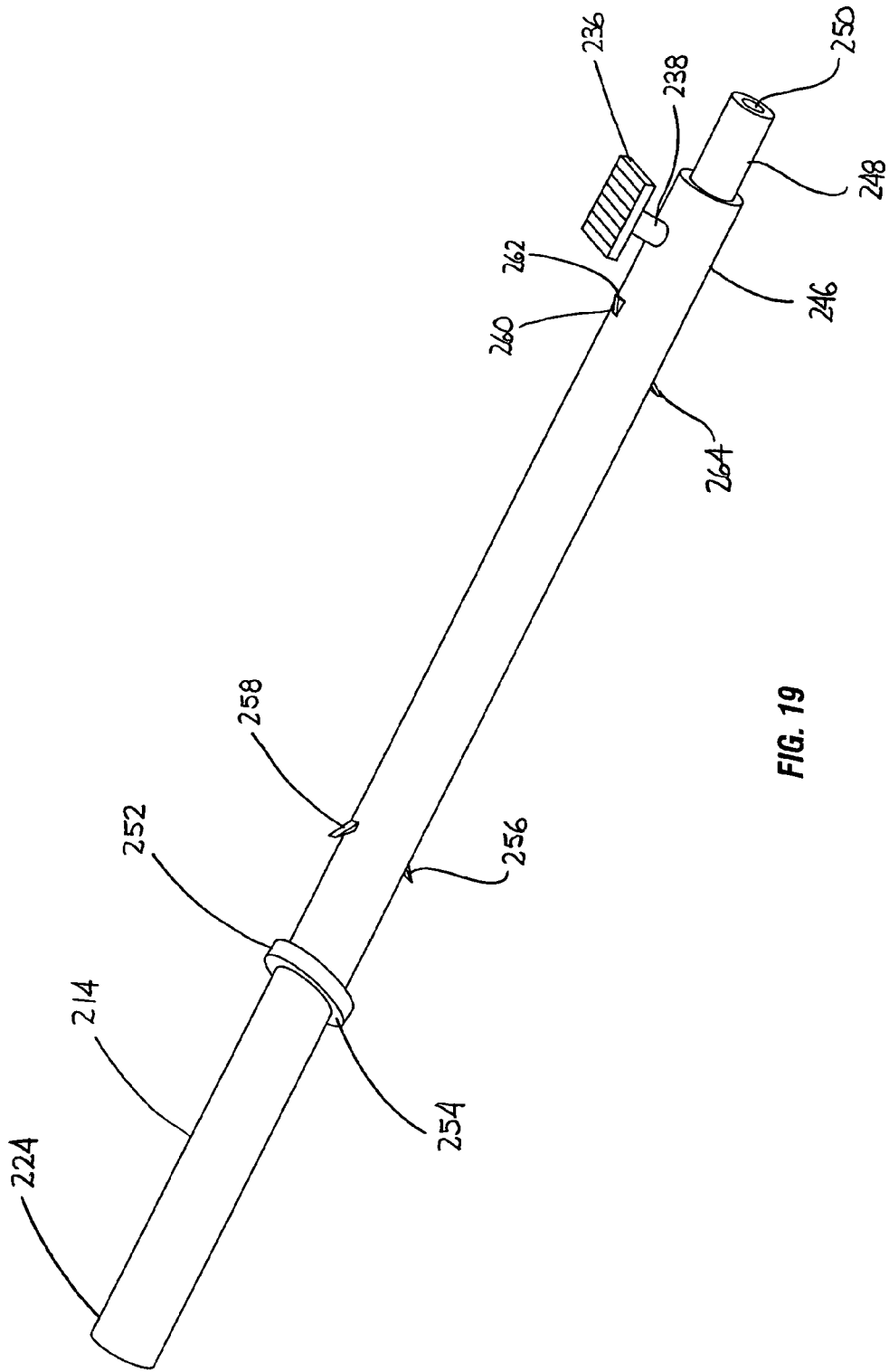
FIG. 19 is a perspective view of a hub of the safety needle shown in FIG. 18, including a lockout mechanism.

Referring also to FIG. 19, hub 214 includes a stepped down portion 248 at proximal end 246. As with prior embodiments, hub 214 includes a through bore 250 allowing needle 216 to be in fluid communication with tube 242. Hub 214 further includes a collar 252 having a distally facing surface 254 for engaging a compression spring to bias hub 214 proximally within elongate outer tubular member 212.

Safety needle 210 includes lockout structure substantially similar to that described with prior embodiments including whiskers 256 and 258. Whiskers 256 and 258 are angled distally to allow whiskers to exit bore 250 and to engage and lock against an outer surface of elongate tubular member 214.

As noted hereinabove, safety needle 210 includes an alternative retraction mechanism 230. Retraction mechanism 230 further includes a lock projection 260 having a proximally facing engagement surface 262. Engagement surface 262 is configured to engage a surface of elongate tubular member 212 and maintain hub 214 in a distal position against the bias of a spring 266. A flexible biasing number 264 is provided on a side of hub 214 opposite to lock projection 260 to bias lock projection 260 into engagement with elongate outer tubular member 212.

Figure 20:
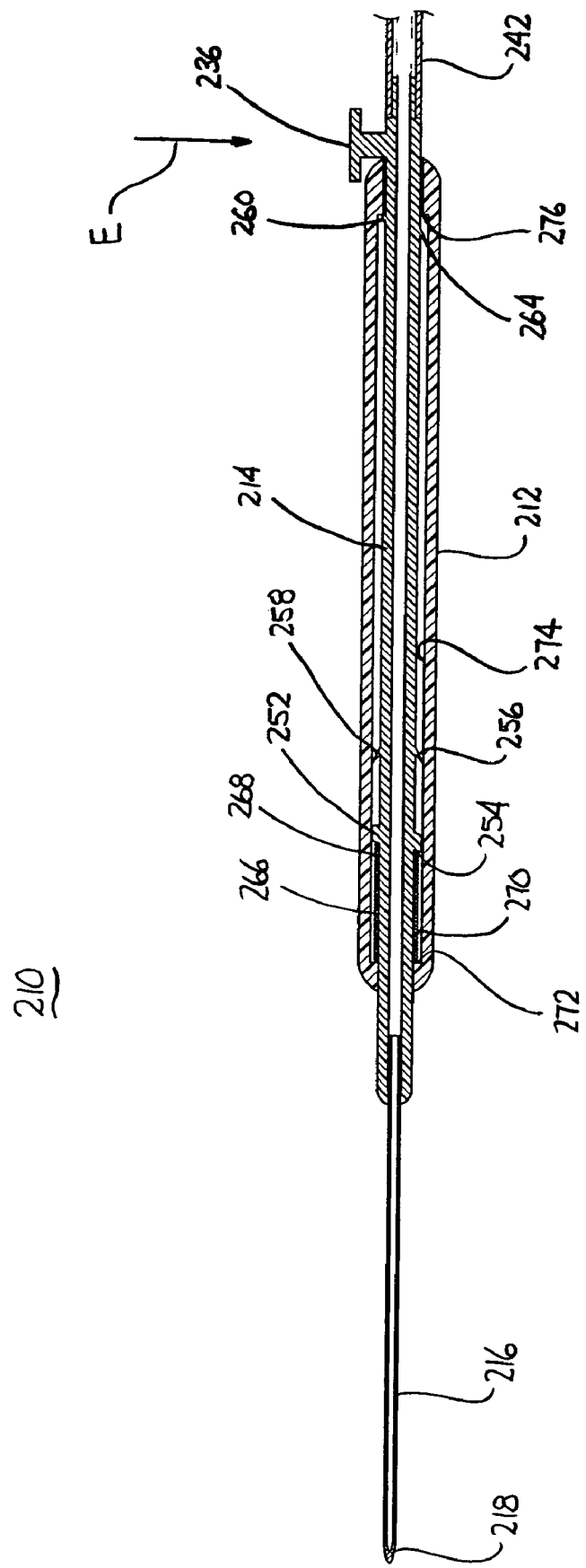
FIG. 20 is a side cross-sectional view of the safety needle shown in FIG. 18 with the needle in the extended position.
Figure 21:
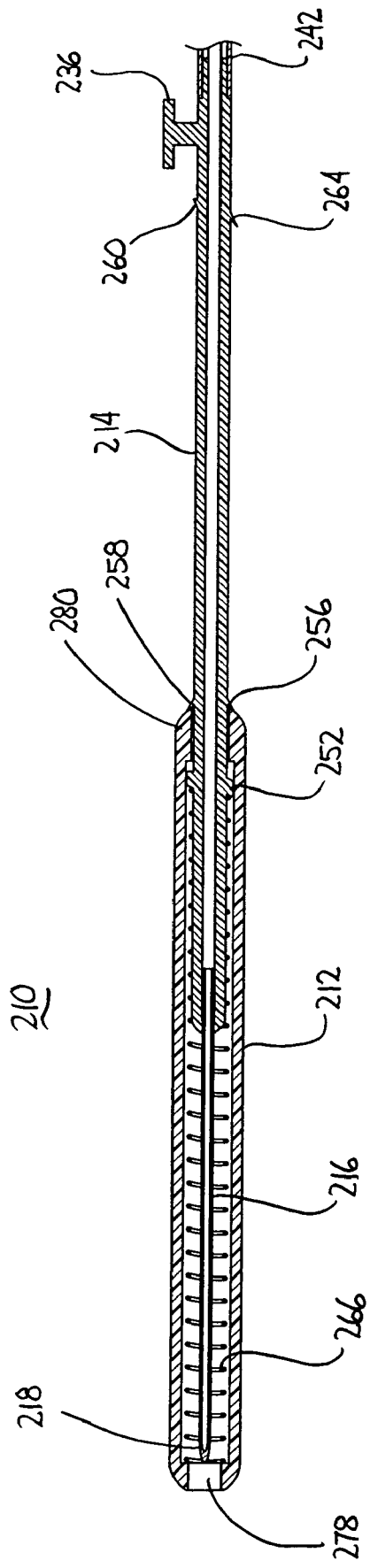
FIG. 21 is a side view of the safety needle shown in FIG. 18 with the needle in the retracted position and the lockout mechanism engaged.

Referring now to FIGS. 20 and 22, further details and the operation of safety needle 210 will now be described. Safety needle 210 includes a spring 266 having a proximal and 268 and a distal end 270. Proximal end 268 engages distally facing surface 254 of collar 252 on hub 214 to bias hub 214 proximally. Similarly, distal end 270 of spring 266 abuts distal inner surface 272 of elongate tubular member 212 to bias hub 214 proximally. As with previous embodiments, whiskers 258 and 256 engage inner surface 274 of elongate tubular member 212 and provide a drag or friction function to control the rate of retraction of hub 214 due to spring 266.

After use in an intravenous procedure, thumb pad 236 is depressed in relation to elongated tubular member 212 in the direction of arrow E in FIG. 20. As noted hereinabove, lock projection 260 engages a surface of elongate tubular member 212. Specifically, proximally facing surface 262 engages a inner proximal surface 276 of elongate tubular member 212 to hold hub 214 in a distal most position against the bias of spring 266. Flexible member 264 holds hub 214 generally upwardly within elongate tubular member 212 to maintain lock projection 216 in engagement with inner proximal surface 276. As thumb pad 236 is depressed relative to elongate tubular member 212, proximal facing surface 262 of lock projection 260 disengages from inner proximal surface 276 to allow hub 214 to move proximally due to the bias of spring 266. Thus, needle 216, and more specifically, sharp tissue penetrating tip 218, are safely withdrawn into throughbore 278 of elongate tubular member 212 to shield the user from needlestick injury.

Similar to previous embodiments, once hub 214 has been fully retracted within elongate tubular member 212, whiskers 256 and 258 exit bore 250 of tubular member 214 and securely engage a proximal outer surface 280 of elongate tubular member 212 to securely "lockout" hub 214 and needle 216 against re-advancement from elongate tubular member 212.

It will be understood that various modifications may be made to the embodiments disclosed herein. For example, the lockout structure may consist of one or a multiplicity of whiskers or flexible members. Further the disclosed lockout structure need not necessarily be a pair of proximally facing flexible whiskers but may include alternative structure on the hub to securely lock the hub relative to the tubular member after full retraction therebetween. Additionally, the disclosed lockout structure is not limited to incorporation in safety needle's having coaxial springs but may also find application in a variety of differently configured safety needle devices. Therefore, the above description should not be construed as limiting, but merely as exemplifications of particular embodiments. Those skilled in the art will envision other modifications within the scope and spirit of the claims appended hereto.

The invention claimed is:

1. A method of preventing the re-advancement of a needle from a housing:
   providing a safety needle having an elongate tubular member, a hub movably mounted within the elongate tubular member, a needle having a sharp tissue penetrating tip extending distally from the hub, a retraction mechanism configured to move the hub relative to the elongate tubular member and at least one blocking member positioned on the hub and engageable with the elongate tubular member;
   actuating the retraction mechanism to move the hub and associated needle proximally within the elongate tubular member; and
   moving the blocking member to a position externally of the elongate tubular member and engaging a proximal end of the elongate tubular member such that the hub can not move distally relative to the elongate tubular member.

2. The method as recited in claim 1, wherein the step of moving includes moving the blocking member along an inner surface of the elongate tubular member to regulate a rate of movement of the hub in relation to the tubular member.

* * * * *